United States Patent [19]

Charlton

[11] Patent Number: 5,786,228
[45] Date of Patent: Jul. 28, 1998

[54] FLUID COLLECTION KIT AND METHOD

[75] Inventor: David Edward Charlton, Sunnyvale, Calif.

[73] Assignee: Biex, Inc., Dublin, Calif.

[21] Appl. No.: 795,964

[22] Filed: Feb. 5, 1997

Related U.S. Application Data

[63] Continuation of Ser. No. 481,611, Jun. 7, 1995, abandoned.

[51] Int. Cl.$^6$ .......................................................... G01N 1/18
[52] U.S. Cl. .......................... 436/177; 436/174; 436/176; 436/180; 422/61; 422/99; 422/101; 422/102; 600/573; 73/64.56; 73/863.21; 73/863.23; 73/864.91; 210/780; 210/359
[58] Field of Search .................................. 436/174, 176, 436/177, 178, 180, 810; 422/61, 99, 100, 101, 102, 104; 206/569; 210/780, 359, 444, 454; 128/760, 769; 73/863.21, 863.23, 864.91, 64.56; 600/573, 580

[56] References Cited

U.S. PATENT DOCUMENTS

| | | | |
|---|---|---|---|
| 3,832,141 | 8/1974 | Haldopoulos | 422/101 |
| 3,846,077 | 11/1974 | Ohringer | 422/100 |
| 4,209,488 | 6/1980 | Breno | 422/101 |
| 4,210,623 | 7/1980 | Breno et al. | 422/101 |
| 4,418,702 | 12/1983 | Brown et al. | 600/573 |
| 4,644,807 | 2/1987 | Mar | 73/864.62 |
| 4,895,808 | 1/1990 | Romer | 436/178 |
| 5,022,409 | 6/1991 | Goldstein et al. | 600/573 |
| 5,103,836 | 4/1992 | Goldstein et al. | 600/573 |
| 5,131,404 | 7/1992 | Neeley et al. | 600/576 |
| 5,215,102 | 6/1993 | Guirguis | 600/584 |
| 5,259,956 | 11/1993 | Mercer et al. | 210/454 |
| 5,268,148 | 12/1993 | Seymour | 422/101 |
| 5,334,502 | 8/1994 | Sangha | 435/7.21 |
| 5,339,829 | 8/1994 | Thieme et al. | 600/573 |
| 5,376,337 | 12/1994 | Seymour | 422/101 |
| 5,447,837 | 9/1995 | Urnovitz | 435/5 |
| 5,479,937 | 1/1996 | Thieme et al. | 600/573 |
| 5,494,646 | 2/1996 | Seymour | 422/101 |
| 5,523,055 | 6/1996 | Hansen et al. | 422/102 X |

OTHER PUBLICATIONS

The Condensed Chemical Dictionary —10th Edition, 1981, p. 1017.

*Primary Examiner*—Marueen M. Wallenhorst
*Attorney, Agent, or Firm*—McDonnell, Boehnen, Hulbert & Berghoff; John McDonnell; David Harper

[57] ABSTRACT

A fluid collection, filtration, and storage device is described. The device has a first tube with a closed first end, an open second end, inner tube-wall surfaces, and an internal diameter; a second tube with a first end porously closed by a filter and an open second end and having an external diameter smaller than the internal diameter of the first tube, the second tube slidably contacting the inner tube-wall surfaces of the first tube at the first end of the second tube when the second tube is inserted in the first tube; and a cap adapted to seal the open second end of the first tube and the open second end of the second tube in a single closing operation while the second tube is inserted into the first tube. The kit is particularly adapted for collecting and storing viscous biologic samples, such as saliva, in the inner tube after the sample has been mixed with a preservative or other substance initially located in the filter.

19 Claims, 2 Drawing Sheets

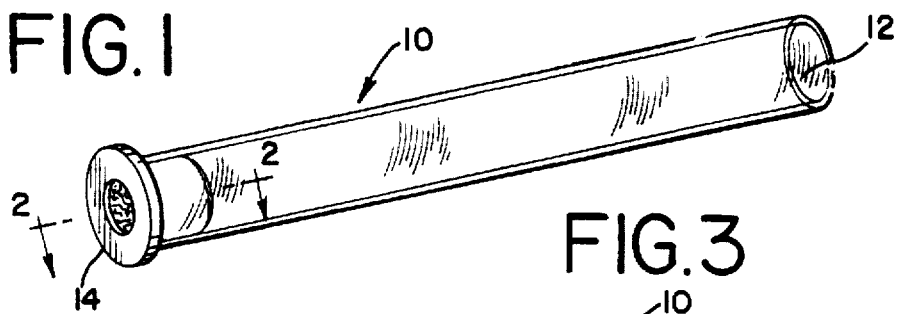
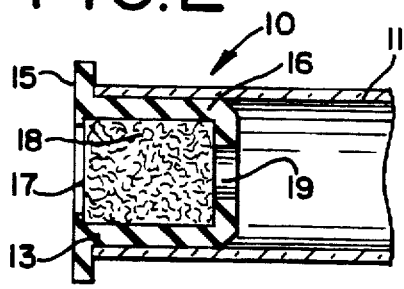
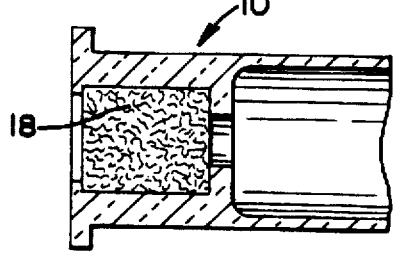
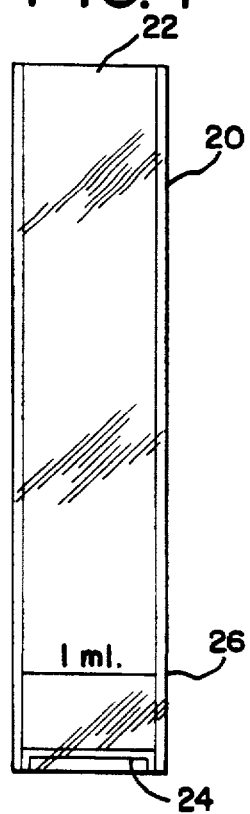
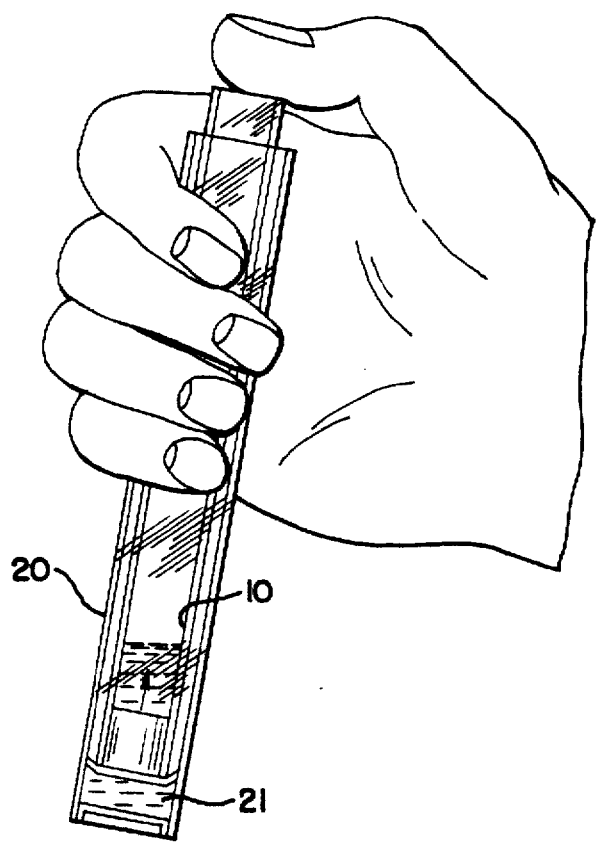

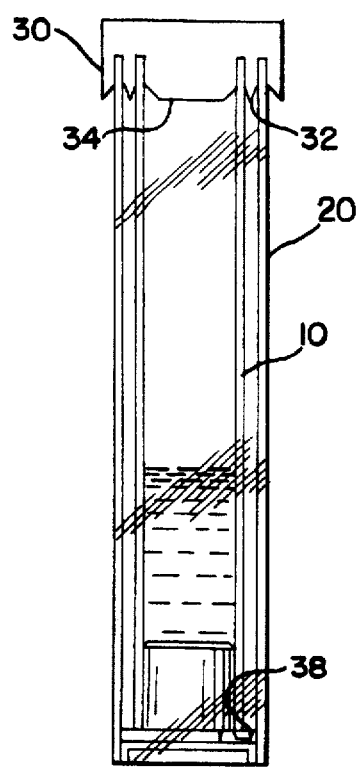
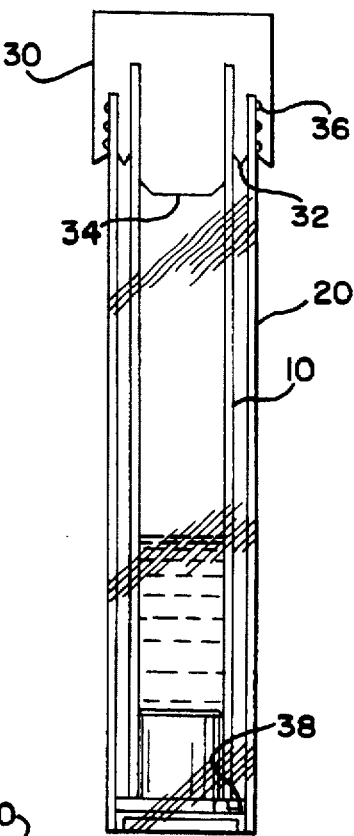
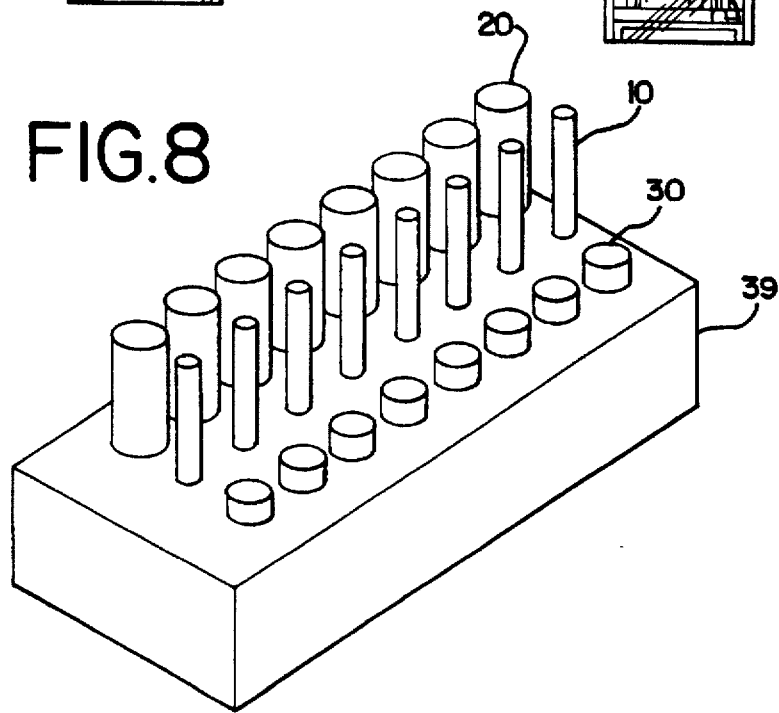

FLUID COLLECTION KIT AND METHOD

CROSS REFERENCE TO RELATED APPLICATIONS

This application is a continuation of U.S. application Ser. No. 08/481,611, filed Jun. 7, 1995 now abandoned.

TECHNICAL FIELD

This invention is in the field of fluid collection kits and in a preferred embodiment is particularly directed to kits used to collect and store viscous fluids while protecting the fluids against bacteriological contamination.

BACKGROUND

The collection and storage of viscous biologic samples, such as saliva, that are subject to degradation by bacteria and other organisms is a common problem. Viscous liquids are difficult to handle in pipettes and other apparatuses normally used with less viscous aqueous samples. The viscosity of the samples also makes it difficult to mix the samples with preservatives in order to protect against biologic breakdown. Such preservatives (or other materials, such as inhibitors of endogenous peptidases or other enzymes present in sample of biologic origin), which are often dried onto the surfaces of a container in which a non-viscous aqueous solution will be collected, cannot diffuse through a viscous liquid and therefore do not protect interior portions of the liquid against bacterial action.

A number of systems have been developed for handling viscous liquids, particularly saliva and blood serum. See, for example, Haldopoulos, U.S. Pat. No. 3,832,141; Ohringer, U.S. Pat. No. 3,846,077; Breno, U.S. Pat. No. 4,209,488; Mar, U.S. Pat. No. 4,644,807; Romer, U.S. Pat. No. 4,895,808; and Seymour, U.S. Pat. No. 5,268,148. However, those apparatuses that have previously been developed in this field are generally sophisticated devices intended for use by a skilled laboratory technician. The present invention was made with an unskilled user in mind, particularly an untrained patient collecting a saliva sample or similar fluid sample at home in the absence of any training or instruction other than written instructions that will accompany a kit. It is this need for a simplified and easy-to-use collection kit for the collection and storage of viscous fluids, such as saliva, that has led to the present invention.

SUMMARY OF THE INVENTION

It is an object of the present invention to provide a kit which allows for simple collection and storage of viscous biologic fluids, such as saliva, as well as other viscous fluids.

It is a further object of the invention to provide a collection system in which a viscous liquid can be thoroughly mixed with a preservative in order to avoid degradation by microorganisms, such as bacteria, that may be present in the sample.

These and other objects of the invention have been accomplished by providing a fluid collection, filtration, and storage device, comprising a first tube having a closed first end, an open second end, inner tube-wall surfaces, and an internal diameter; a second tube having a first end porously closed by a filter and an open second end and having an external diameter smaller than the internal diameter of the first tube, the second tube further slidably contacting the inner tube-wall surfaces of the first tube at least at the first end of the second tube when the second tube is inserted in the first tube; and a cap adapted to seal the open second end of the first tube and the open second end of the second tube in a single closing operation while the second tube is inserted into the first tube. The kit is particularly adapted for collecting and storing viscous biologic samples, such as saliva, in the inner tube after the sample has been mixed with a preservative or other substance located in the filter, such as a dye or protease inhibitor.

BRIEF DESCRIPTION OF THE DRAWINGS

The invention will be better understood by reference to the following description of specific embodiments in combination with the drawings that form part of the specification, wherein:

FIG. 1 is a perspective view of an inner fluid filtration and storage tube that forms part of the apparatus of the invention. In this figure, line 2—2 shows the plane of view in FIG. 2.

FIG. 2 is a plan view of a first embodiment of the inner collection tube of the apparatus of the invention.

FIG. 3 is a plan view of a second embodiment of the inner collection tube showing the same view presented in FIG. 2.

FIG. 4 is a plan view of an outer fluid collection tube of an embodiment of the invention.

FIG. 5 is a perspective drawing showing the interaction of the inner tube and the outer tube when fluid is being transferred from the outer collection tube to the inner collection tube.

FIG. 6 is a plan view of a first embodiment of the invention showing a cap sealing both the inner and the outer tubes of an embodiment of the invention.

FIG. 7 is a plan view of a second embodiment showing a second cap sealing both the inner and outer collection tubes.

FIG. 8 is a perspective view of a fluid collection kit.

DESCRIPTION OF SPECIFIC EMBODIMENTS

Referring now in detail to the embodiments shown in the drawings for the purpose of illustrating the present invention, the same numbers are used to show corresponding elements of the different embodiments in the different drawings.

The apparatus of the invention comprises two tubes that fit within one another. The inner tube 10, referred to as the filtration and storage tube, is shown in FIG. 1 in a perspective view. Although this embodiment is shown as a tube having a circular cross-section, the cross-section can be in any shape as long as the inner tube fits within the later-described outer tube. The inner tube has two ends, an open end 12 and a porously closed end 14. By "porously closed" is meant that a porous material is present in the end 14 of tube 10 so that a liquid can penetrate through the pores of the porous material, which will act both as a filter and as a mechanical means for breaking up polymeric materials that may be contributing to viscosity, such as mucopolysacarides in saliva. On the other hand, the "porously closed" end blocks the passage of solids, including particulate solids larger in size than the pores.

A detail of the porous closure is shown in FIG. 2. In this first embodiment, collection and storage tube 10 is formed from a simple glass or plastic tube 11, an annular elastomeric plug 13, and a porous passageway defined by an external opening 17, a porous plug 18 entrapped in annular elastomeric plug 13, and an internal passageway 19. In this embodiment elastomeric plug 13 has a lip 15 which contacts the inner surfaces of the outer collection tube (to be described in connection with FIG. 4).

FIG. 3 shows an alternative embodiment from the same view shown in FIG. 2. In this embodiment all of the portions of collection and storage tube 10 formed in FIG. 2 by tube 11 and elastomeric plug 13 are formed as a unitary device, such as can be produced from molded plastic. Porous plug 18 is then inserted in the passageway to provide the porous closure described above. Alternatively, the central portion of the porous end of collection and storage tube 10 can be formed from the same material as the walls as an integral filter (e.g., by injecting air or inert liquids in this region during the molding process).

FIG. 4 shows an embodiment of the outer tube 20, referred to as a sample collection tube. This tube has an open end 22 and a permanently closed end 24. In preferred embodiments, a volume marker can be inscribed or otherwise marked on the outside of the container, such as is shown at 26 of FIG. 4.

FIG. 5 shows the two tubes of the apparatus in use. A sample 21 has been collected in outer tube 20. Inner tube 10 is being forced by hand pressure into outer tube 20, forcing sample 21 through the porous filter and into the interior of inner tube 10.

In preferred embodiments of the invention, the exterior bottom of inner tube 10 is shaped to tightly contact the interior bottom of external tube 20 so that space 38 between the two tubes is at a minimum when inner tube 10 has been forced to the bottom of outer tube 20. The space 38 is generally less than 20 µl, preferably less than 10 µl, and more preferably less than 5 µl. This provides for maximum transfer of fluid into the storage portion of inner tube 10.

As shown in FIG. 6, cap 30 closes both the inner tube 10 and outer tube 20 in a single closure operation. In this embodiment, a press fit is provided by an inner plug 34 that fits into the open end of inner tube 10 and an annular ring 32 that fits between the inner and outer tubes. The press fit is preferably tighter for the outer tube and looser for the inner tube so that the two tubes do not separate from each other during removal of cap 30.

An alternative embodiment for a cap and storage system is shown in FIG. 7. In this embodiment inner tube 10 is somewhat longer than outer tube 20 and internal plug 34 projects somewhat from the bottom of cap 30, thereby allowing the cap to be inserted first into the inner tube for ease of handling. Annular ring 32 operates in the same manner, but the cap is secured to the outer tube 20 by a screw-type closure 36 with matching threads on cap 30 and outer tube 20. As before, the inner tube is held in place by a loose press fit. Similar variations in cap structure will be apparent to those skilled in container technology from these examples.

Piston-like filtration systems similar to that shown in FIG. 5 exist in the prior art, but not in a permanent collection and storage system. For example, U.S. Pat. No. 3,832,141, which is herein incorporated by reference, shows an inner filter tube and outer collection tube similar in some ways to the apparatus of the invention. However, the apparatus is not designed to collect and store samples and indeed is specifically designed so that the inner and outer tubes can be separated from one another after sample is collected in the inner tube. A similar system is also shown in FIGS. 23-26 of U.S. Pat. No. 5,268,148. Again, the system is not designed for storage of samples and further contains a blotter for saliva located in the outer tube that exemplifies many of the disadvantages of the prior art. In fact, most if not all of the prior art devices show a porous blotter of some type that is used to collect saliva samples. While such pads can readily be used to collect saliva by inserting the pad into the mouth of a patient, it is impossible to measure accurately the amount of fluid that is collected on such a porous material. For example, a patient with a dry mouth might only poorly wet a porous pad, while a patient with normal saliva flow might provide two or more times as much saliva on the same-sized pad. In contrast, the simple outer collection tube 20 of the present invention, with an optional mark 26 showing the desired volume of sample, allows a known volume of saliva to be collected. By providing a piston-like filtering and collection tube 10 that fits closely into the collection vial, all or nearly all of the sample can be forced through the porous filter at the end of the collection tube 10 and into the inner collection tube, where the sample will remain as shown in FIGS. 6 and 7. Since this sample has been forced through porous plug (filter) 18, the apparatus of the present invention provides for thorough mixing of the sample with any soluble material located on filter 18 that might be desired to be mixed with the sample. For example, a preservative to protect biological fluids against degradation can be included in the filter. While prior collection devices for non-viscous fluids have provided for a soluble material coated on the walls of a collection container, such a system would not be appropriate for viscous fluids, such as those intended to be the samples used in the devices of the present invention. Diffusion occurs only slowly in viscous samples, and a preservative or other material coated on the walls of a collection vial would not readily penetrate to all portions of a sample. This is particularly true in saliva, which contains mucopolysacarides and glycoproteins, which impede diffusion. These materials also sometimes coagulate into web-like structures that further impede diffusion. By forcing saliva or a similar fluid through a porous disk or filter as described above, not only will the saliva be well mixed with a preservative or other chemical agent located in dry form on the filter, but the mucopolysacarides and glycoproteins will be broken up to provide for a less viscous fluid when the saliva is present in the inner collection tube.

The filter or porous plug used in the apparatus of the invention can be selected for the particular viscosity and type of sample being collected. The variety of pore sizes and void volumes that can be used can be seen when considering saliva as an example. Pore sizes of less than 1 micron have been shown to work, while 100 micron pores also appear to be useful, although near the limit for breaking up mucopolysacarides and glycoproteins as described above. Pore sizes in the 25–50 micron range are preferred to avoid the clogging that sometimes occurs with smaller pore sizes. However, a 2-part filter with an external coarse filter over a 1 micron inner filter would work satisfactorily, as the external coarse filter would prevent clogging of the finer internal filter.

The closeness of fit with which the internal tube contacts the external tube will vary depending on the viscosity of the fluid and the coarseness of the filter. The primary characteristic of fit required for good operation is that the filter is sufficiently porous to provide less fluid resistance to the desired sample collected in the outer tube than the fluid resistance that is present at the locations where the two tubes slidably contact each other. Elastomeric materials are preferred for the slidable contact, since they do not require close manufacturing tolerances. However, if manufacturing tolerances are high, even rigid materials can be used to provide the slidable contact.

Although the examples above show tubes with circular cross-sections and corresponding piston-like structures of circular shapes, other shapes are possible as long as the inner tube or some portion thereof such as the elastomeric plug shown in FIG. 2 slidably contacts the interior surfaces of the outer tube at all locations so that sample is forced through the porous filter and does not escape around the edges of the inner tube where the inner tube contacts the interior walls of the outer tube.

Any number of materials can be present on the filter so that they will mix with the sample, depending on the particular sample being collected. For biological samples, this will generally include a preservative. Examples of preservatives include sodium azide (NaN$_3$) and a combination of 5-chloro-2-methyl-4-isothiazolin-3-one and 2-methyl-isothiazolin-3-one (PROCLIN™). A particularly preferred preservative for saliva is thimerosal. The general operating characteristics of the preservatives are that they be soluble in the fluid with which they are to be mixed and be sufficiently stable to storage under the conditions under which the collection kit will be used. Since these conditions will vary with the sample and with the manner in which sample is collected, a wide variety of agents can be used. For example, a collection kit designed for home use can be refrigerated, which will provide for relatively mild storage conditions and allow reasonably delicate preservatives to be used. A test kit designed for field operation may be subject to a variety of different temperatures and humidities and thus would restrict the preservatives used in such a kit.

Other materials that can be present on the filter include a dye, which makes it possible to readily determine whether uniform mixing has taken place. Examples of dyes include any of the numerous standard dyes set forth in standard dye catalogues, selected to be soluble in the material being collected. A dye particularly useful for saliva collection is FDC Blue #1. The essential characteristic of the dye is that it be soluble in the liquid being collected.

The individual collection apparatuses of the invention can be stored in a fluid collection kit comprising multiple tubes of the two types described above and multiple caps as depicted in FIG. 8. The kit will normally comprise a container 39 adapted to hold the tubes and caps in a readily accessible manner (typical of the type used in a test tube rack in which the individual tubes are inserted into holes in a rack-like device, typically made of cardboard in a commercial collection kit). The individual tubes can have built-in labels for ease of use (for example, containing spaces for patient name and date and time of collection), and written instructions adapted for the particular type of sample can be included in the box that holds the individual tubes.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A fluid collection, filtration, and storage device, comprising:
   a first tube having a closed first end, an open second end, inner tube-wall surfaces, and an internal diameter wherein said first tube is adapted to collect a fluid therein and wherein said first tube does not contain any material that absorbs liquid at variable volumes;
   a second tube having a storage portion and having a first end porously closed by a filter and an open second end and having an external diameter smaller than said internal diameter of said first tube, said second tube further slidably contacting said inner-tube-wall surfaces of said first tube at said first end of said second tube when said second tube is inserted in said first tube so as to transport fluid collected in said first tube through said filter and into the storage portion of said second tube; and
   a cap adapted to seal said open second end of said first tube and said open second end of said second tube in a single closing operation while said second tube is inserted into said first tube to form a closed storage device, said storage device thereby providing said storage portion capable of containing a fluid trapped in said storage portion of said second tube.

2. The device of claim 1, wherein said filter is integrally manufactured with said first end of said second tube.

3. The device of claim 1, wherein said filter is sufficiently porous to provide less fluid resistance to a fluid located in said first tube than fluid resistance at a location where said second tube slidably contacts said first tube.

4. The device of claim 1, wherein said filter has pores with an effective diameter of less than 100 microns.

5. The device of claim 1, wherein said filter has pores with effective diameters from 1 to 50 microns.

6. The device of claim 1, further comprising a preservative located in said filter.

7. The device of claim 6, wherein said preservative is soluble in saliva.

8. The device of claim 7, wherein said preservative is thimerosal.

9. The device of claim 1, further comprising a dye located in said filter.

10. The device of claim 9, wherein said dye is soluble in saliva.

11. The device of claim 10, wherein said dye is a blue dye.

12. The device of claim 1, wherein said second tube is substantially equal in length to a distance measured internal of said first tube from said closed first end to said open second end of said first tube.

13. The device of claim 1, wherein said cap further comprises screw threads and said first tube further comprises screw threads at said open end of said first tube that match said cap screw threads.

14. The device of claim 1, wherein said cap closes said first and second tubes with a friction fit.

15. The device of claim 1, wherein an interior surface of said cap comprises an annular projection that fits between said open end of said first tube and said open end of said second tube.

16. A fluid collection kit, comprising:
   multiple first tubes according to claim 1;
   multiple second tubes according to claim 1;
   multiple caps according to claim 1; and
   a container adapted to hold said first and second tubes and said caps.

17. The device of claim 1, wherein said filter is positioned in a tubular sealing to form an annular plug, said plug having a flange that slidably contacts said inner tube-wall surfaces of said first tube when inserted into said open second end of said first tube.

18. A method of collecting and storing a fluid, comprising:
   collecting a fluid in a first tube having a closed first end, an open second end, inner tube-wall surfaces, and an internal diameter wherein said first tube does not contain any material that absorbs liquid at variable volumes;

inserting into said first tube an internal filtering and holding device comprising a second tube having a storage portion and having a first end porously closed by a filter and an open second end and having an external diameter smaller than said internal diameter of said first tube, said second tube further slidably contacting said inner-tube-wall surfaces of said first tube at said first end of said second tube when said second tube is inserted in said first tube, whereby fluid collected in said first tube is forced through said filter into said second tube; and sealing said first tube and said second tube with a cap adapted to seal said open second end of said first tube and said open second end of said second tube in a single closing operation to form a closed storage device, said storage device thereby containing said fluid trapped in said storage portion of said second tube.

19. The method of claim 18, wherein said fluid is collected in said first tube to a predetermined volume mark on said tube.

* * * * *